(12) United States Patent
Hara

(10) Patent No.: US 7,942,528 B2
(45) Date of Patent: May 17, 2011

(54) PERIMETER

(75) Inventor: Takuya Hara, Shizuoka-ken (JP)

(73) Assignee: Kowa Company, Ltd., Aichi (JP)

( * ) Notice: Subject to any disclaimer, the term of this patent is extended or adjusted under 35 U.S.C. 154(b) by 0 days.

(21) Appl. No.: 12/559,640

(22) Filed: Sep. 15, 2009

(65) Prior Publication Data
US 2010/0002192 A1    Jan. 7, 2010

(30) Foreign Application Priority Data

Oct. 6, 2008 (JP) ................................ 2008-259268

(51) Int. Cl.
*A61B 3/02* (2006.01)
(52) U.S. Cl. ........................................ 351/224; 351/226
(58) Field of Classification Search .................. 359/200, 359/224, 226, 237, 239, 206
See application file for complete search history.

(56) References Cited

U.S. PATENT DOCUMENTS

| | | | |
|---|---|---|---|
| 4,854,694 A | 8/1989 | Hirano et al. | |
| 5,459,536 A | 10/1995 | Shalon et al. | |
| 5,737,060 A | 4/1998 | Kasha, Jr. | |
| 5,946,075 A | 8/1999 | Horn | |
| 2004/0057013 A1 | 3/2004 | Cappo et al. | |

FOREIGN PATENT DOCUMENTS

| | | |
|---|---|---|
| JP | S62-9330 | 2/1987 |
| JP | H4-3213 | 1/1992 |
| JP | 2002-272685 | 9/2002 |

OTHER PUBLICATIONS

EP Search Report—Sep. 20, 2009, Kowa Company.

*Primary Examiner* — Jack Dinh
(74) *Attorney, Agent, or Firm* — Duane Morris LLP

(57) ABSTRACT

A perimeter has fixation state judging means for individually judging a fixation state of an examinee in connection with each presented stimulus, and the fixation state judging means individually judges the fixation state whenever the stimulus is presented. Even if defective fixation is judged, retest is conducted on only a point where the stimulus was presented, which was judged to be defective fixation. Then, examiner's burden and examinee's burden can be lightened, the test time can be made shorter and test efficiency can be improved in comparison with a case where the whole test is retried from the first as a conventional way.

4 Claims, 7 Drawing Sheets

(a)

(b)

(a)

NORMAL THRESHOLD PERIMETRY

F I G. 7
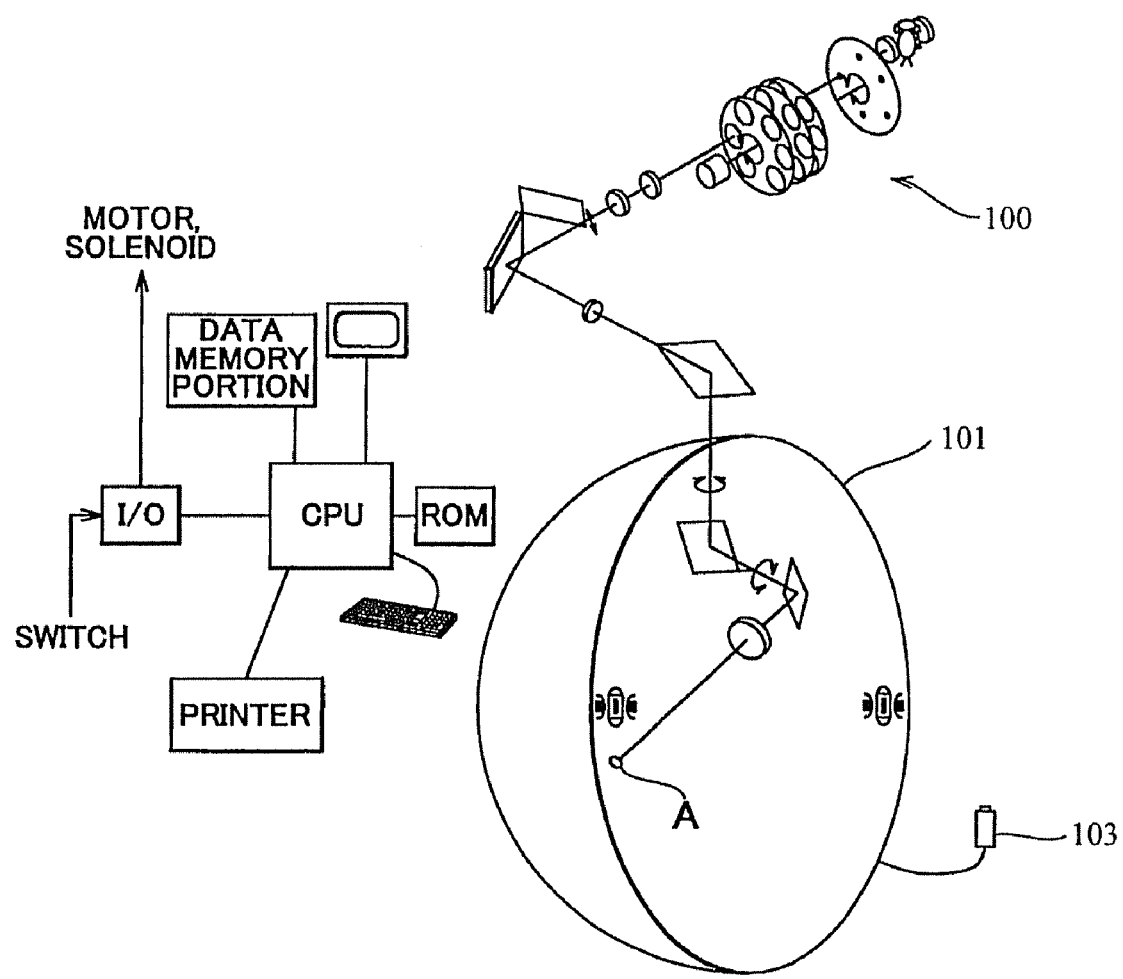

PERIMETER

CROSS REFERENCE TO RELATED APPLICATION

The present disclosure relates to subject matter contained in Japanese patent application No. 2008-259268 filed on Oct. 6, 2008, the disclosure of which is expressly incorporated herein by reference in its entirety.

BACKGROUND OF THE INVENTION

This invention relates to a perimeter for measuring a visual field of an examinee in such a state that the examinee fixates a predetermined fixation point.

BACKGROUND ART

When suffering from an ophthalmic disease, such as glaucoma and hemianopsia, it is known that a person has a visual field contraction or a visual field defect. For these reasons, perimeters having various structures have been proposed as devices for finding such diseases (see Japanese patent application the publication number of which is 2002-272685).

FIG. 7 is a typical view showing a structure of a conventional perimeter. In FIG. 7, a reference numeral 100 denotes a projection optical system for projecting stimuli A, and a reference numeral 101 denotes a visual field dome in the shape of a semi-sphere for projecting stimuli thereon. And, a reference numeral 103 denotes a response switch to be operated by an examinee. When executing perimetry in such a state that an examinee fixates a fixation target (stimulus which is located at a center of visual field) inside the visual field dome 101, the projection optical system 100 successively displays stimuli A at various positions of the visual field dome 101. An examinee operates the response switch 103 when perceiving the stimulus A, but does not operate the response switch 103 when not perceiving. The visual field of an examinee can be measured based upon the response from the examinee.

An important point for executing a correct perimetry is that an examinee correctly fixates a fixation target. Especially, it may be difficult for elderies or persons having eye disorders to continue to fixate a fixation target during a test, and it is necessary to judge as to whether or not an examinee correctly fixates a fixation target in order to execute correct perimetry.

Units having various kinds of structures have been proposed as units for judging a fixation state of an examinee (see Japanese patent applications publication Nos. S62-9330 and H4-3213).

However, a conventional perimeter has such a problem that if an examinee does not correctly fixate a fixation target at a predetermine probability, credibility on all examination points in the perimetry is judged to be low and it is necessary to retry the perimetry thereby. In such a case, some burdens are forced on an examiner or an examinee, and examination time is longer thereby.

Under the above-mentioned circumstances, an object of the invention is to provide a perimeter for solving the above-mentioned problems.

SUMMARY OF THE INVENTION

One aspect of the invention exemplarily shown in FIGS. 1 and 2 is a perimeter for measuring a visual field in a state that an examinee fixates a predetermined fixation point, comprising:

stimulus presentation means for successively presenting stimuli having predetermined luminance at various positions in a visual field of an examinee;

operation means to be operated by said examinee who perceived said presented stimulus;

visual field judging means for judging said visual field of said examinee based on signals from said stimulus presentation means and said operation means; and fixation state judging means for individually judging fixation state of said examinee in connection with each presented stimulus.

Another aspect of the invention is the perimeter, wherein said fixation state judging means has fixation state detecting portion for detecting a fixation state of an examinee, criterion outputting portion for outputting criterions for judgment of said fixation state, comparison judging portion for judging said fixation state by comparing signals from said fixation state detecting portion and said criterion outputting portion with each other, and judged result output portion for outputting judged result in connection with each presented stimulus based upon signals from said stimulus presentation means and said comparison judging portion.

Another aspect of the invention is the perimeter, wherein said fixation state detecting portion is comprised of a photographing portion for obtaining successive images by photographing a front eye portion of an examinee and an image processing portion for processing said images obtained by said photographing portion so as to extract a pupil of said examinee and obtaining a center of said pupil, and said comparison judging portion judges a fixation state by comparing said center of pupil computed by said image processing portion with said criterion.

Another aspect of the invention is the perimeter, further comprising monitor means for displaying a judged result of a visual field in connection with each presented stimulus and a judged result of said fixation state in connection with each presented stimulus.

Another aspect of the invention is the perimeter, further comprising judgment processing means for controlling said stimulus presentation means to present a stimulus again to a measurement point where "defective fixation" was judged by said fixation state judging means.

Another aspect of the invention is the perimeter further comprising judgment processing means for controlling said stimulus presentation means to detect defective fixation by stimulating a blind-spot on said measurement point where "defective fixation", "may be defective fixation" or "no defective fixation" was judged by said fixation state judging means, whereby a blind-spot is stimulated for said measurement point where "defective fixation" was judged without fail, a blind-spot is stimulated at a first probability for said measurement point where "may be defective fixation" was judged, and a blind-spot is stimulated at a second probability ($0 \leq$ the second probability $<$ the first probability) for said measurement point where "no defective fixation" was judged.

According to these aspects of the invention, the fixation state is not judged in the whole perimetry, but the fixation state is individually judged for each stimulus in connection with each presented stimulus. In other words, the measurement point having high credibility and the measurement point having low credibility can be discriminated from each other. Then, even if defective fixation is judged, it is sufficient to retest only the point where the stimulus was presented, which was judged to be defective fixation. Therefore, examiner's burden and examinee's burden are lighter than a case where the whole test is retried from the first as a conventional way, and the test time is shorter and the test efficiency is improved thereby.

BRIEF DESCRIPTION OF THE DRAWINGS

FIG. 7 is a typical view which shows an example of a structure of a conventional perimetry.

BEST MODE FOR CARRYING OUT THE INVENTION

Figure 1:
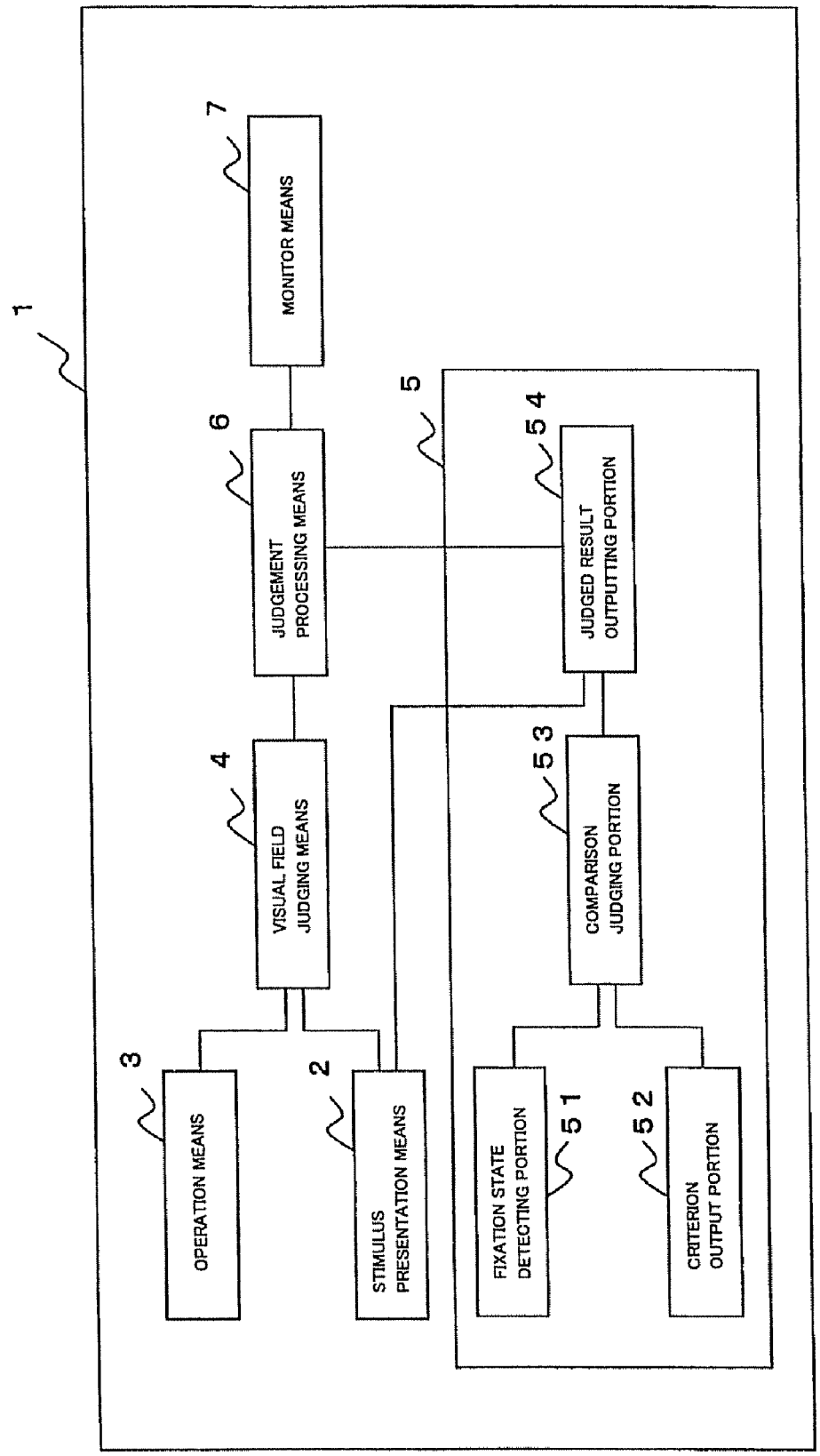
FIG. 1 is a block diagram which shows an example of a structure of a perimeter according to the invention.
Figure 2:
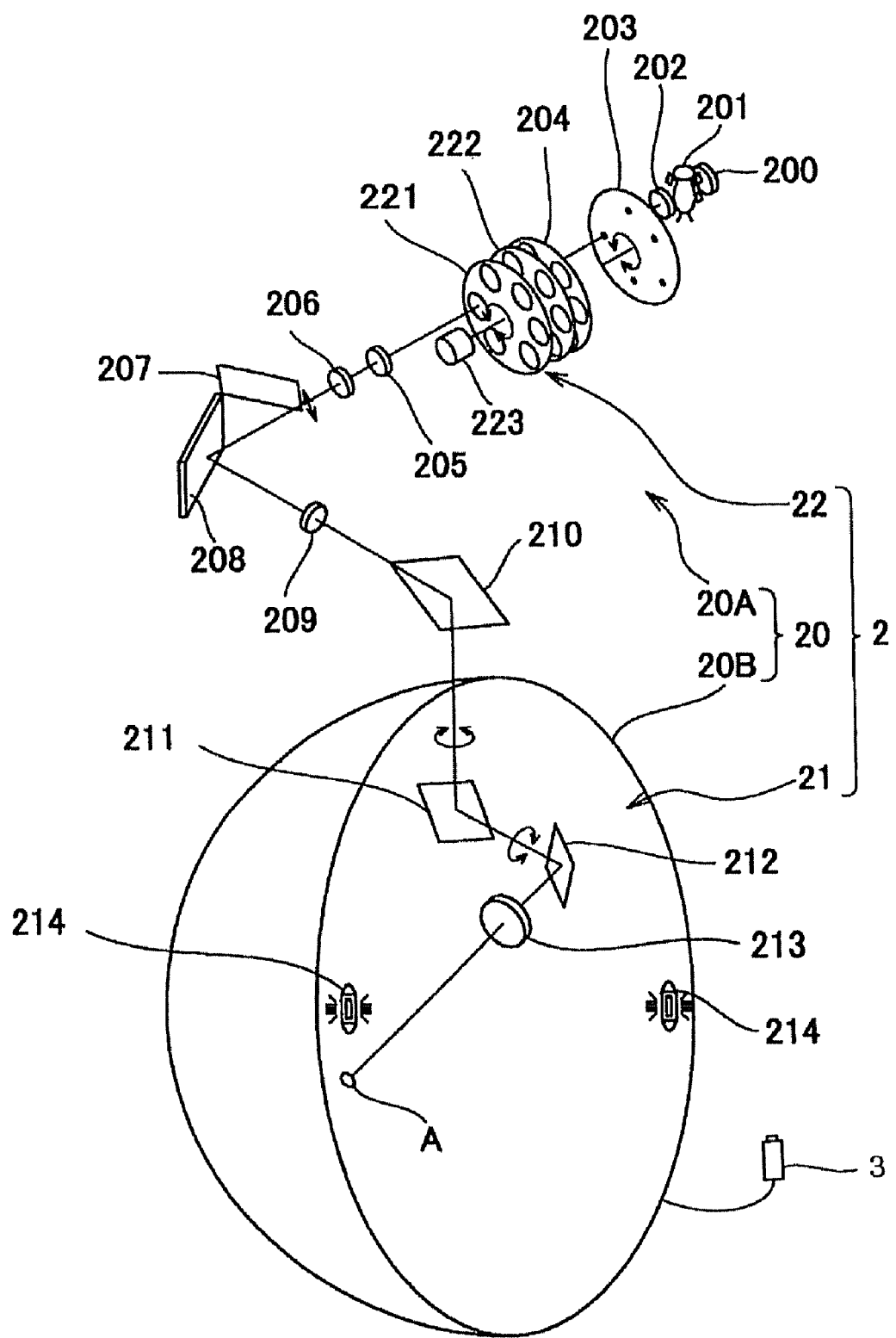
FIG. 2 is a typical view which shows an example of stimulus presentation means to be used in the perimeter according to the invention.
Figure 3:
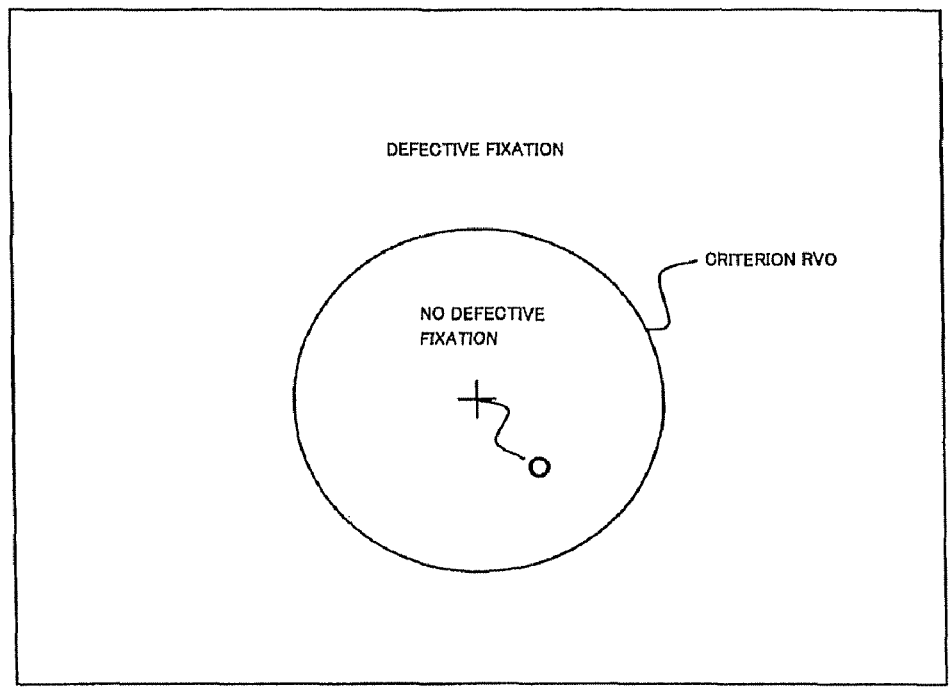
FIG. 3(a) is a typical view for explaining a way of judgment as to whether there is defective fixation or not from a center position of a pupil.
FIG. 3(b) is a typical view for explaining a way of judging "defective fixation", "may be defective fixation" or "no defective fixation" from a center position of a pupil.
Figure 3:
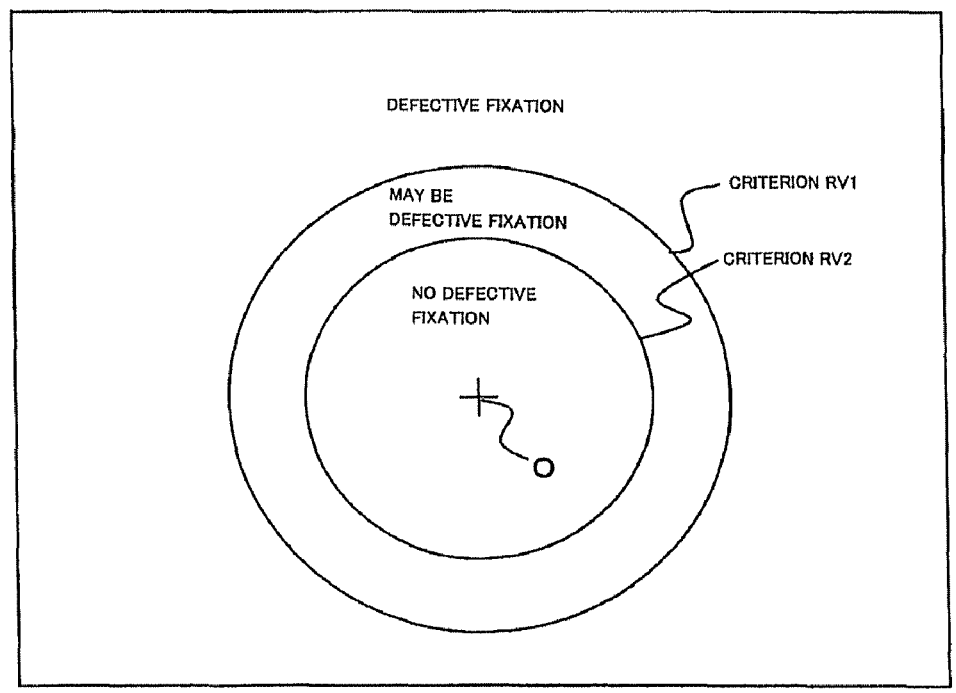
Figure 4:
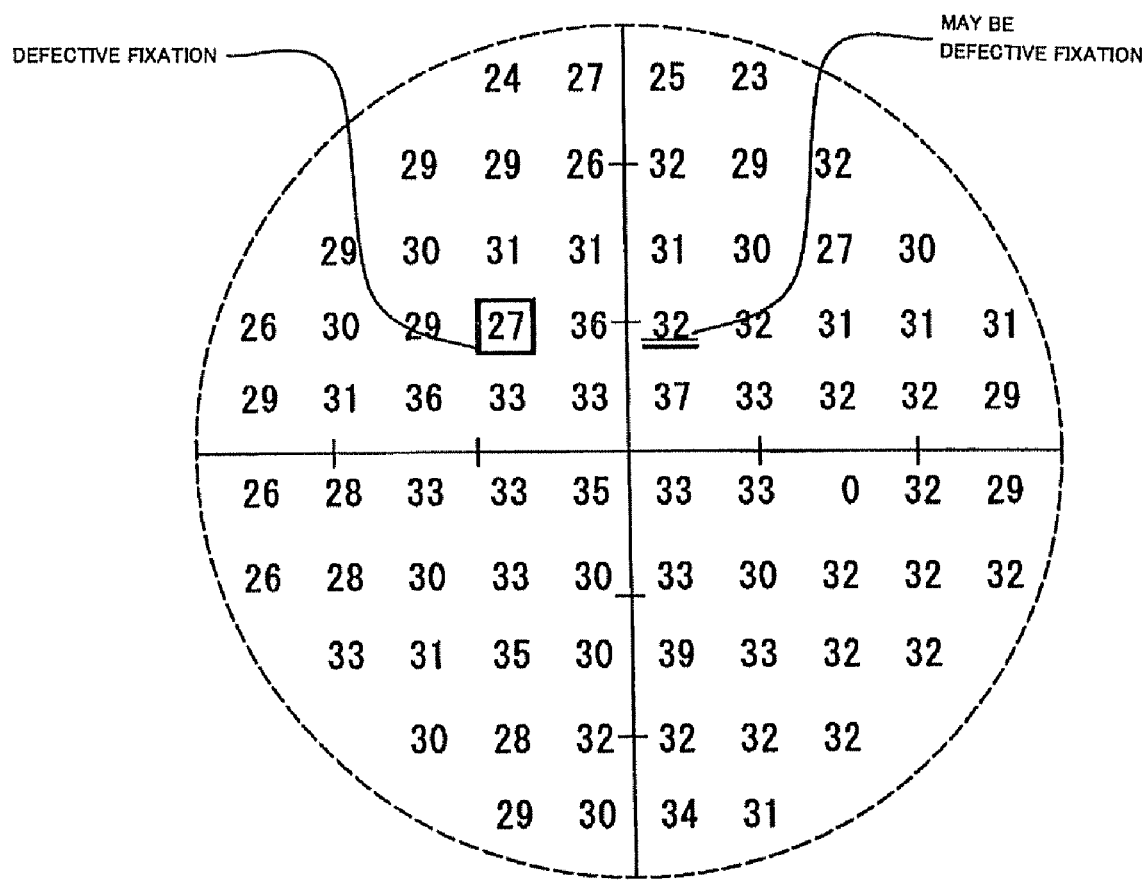
FIG. 4 is a typical view which shows an example of presentation through monitor means.
Figure 5:
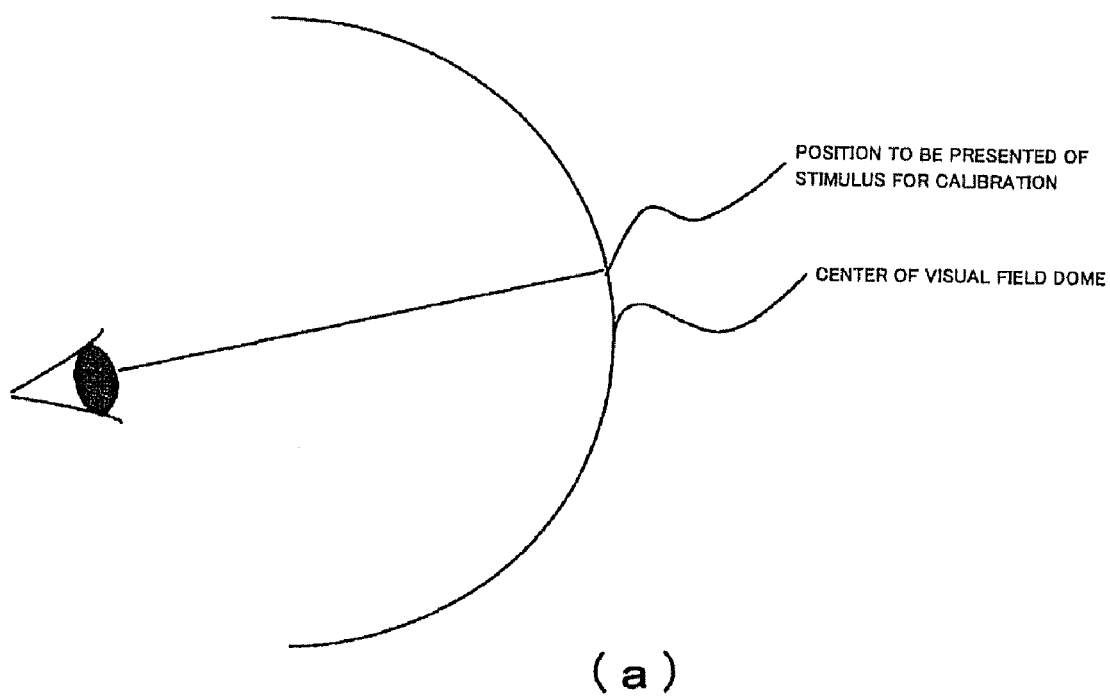
FIG. 5 is a typical view for explaining calibration of a position of rotation center of an eyeball.
Figure 5:
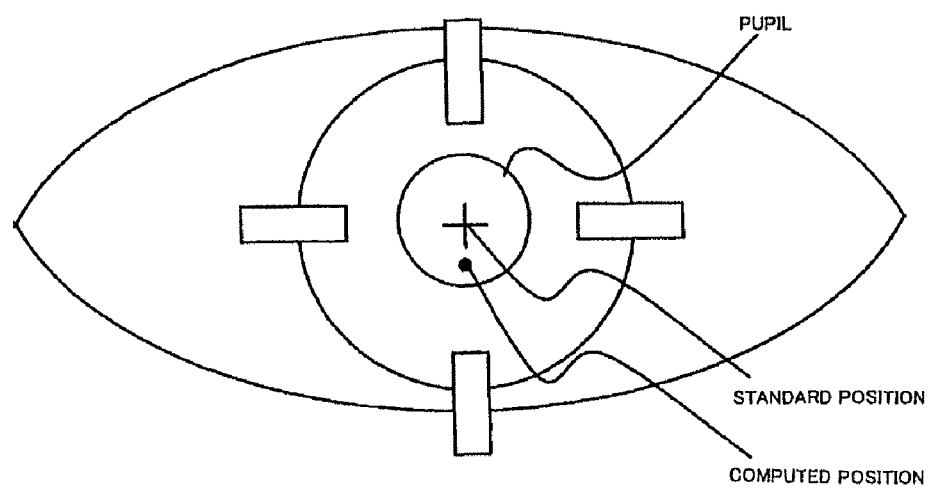
Figure 6:
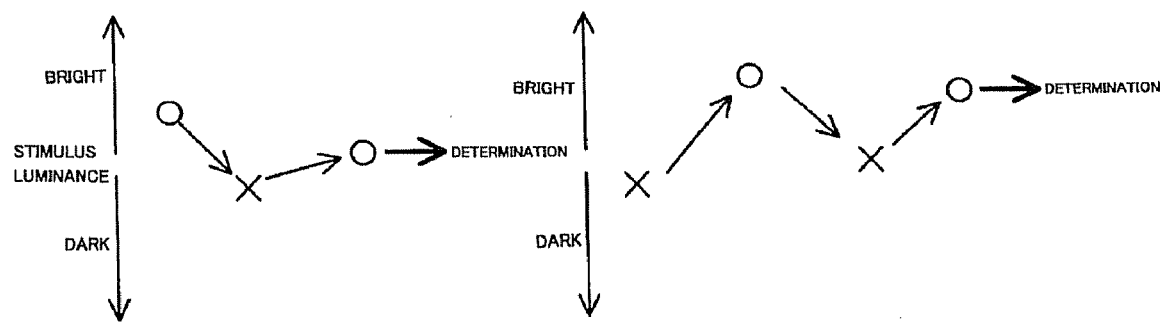
FIG. 6 is a typical view for explaining subjects for fixation state judgment in a threshold perimetry.

A best mode for executing the invention is now described, referring to FIGS. 1 to 6. FIG. 1 is a block diagram which shows an example of a structure of a perimeter according to the invention, FIG. 2 is a typical view which shows an example of stimulus presentation means to be used in the perimeter according to the invention, FIG. 3(a) is a typical view for explaining a way of judgment as to whether there is defective fixation or not from a center position of a pupil, FIG. 3(b) is a typical view for explaining a way of judging "defective fixation", "may be defective fixation" or "no defective fixation" from a center position of a pupil, FIG. 4 is a typical view which shows an example of presentation through monitor means, FIG. 5 is a typical view for explaining calibration of a position of rotation center of an eyeball, and FIG. 6 is a typical view for explaining subjects for fixation state judgment in a threshold perimetry.

A perimeter according to the invention, which is exemplarily denoted with reference number 1 in FIG. 1, measures a visual field of an examinee in such a state the examinee fixates a fixation point (such as a central point of a visual field dome). Such a perimeter 1 has stimulus presentation means 2 for successively presenting the stimuli with a predetermined luminance at various positions in a visual field of an examinee. Preferably, the stimulus presentation means 2 as shown in FIG. 2 is used (details are described hereinafter).

The perimeter 1 has operation means 3, such as a push switch, and an examinee can operate the operation switch 3 when perceiving the presented stimulus A.

The perimeter 1 according to the invention has visual field judging means 4 for judging the visual field of an examinee based upon signals from the stimulus presentation means 2 and the operation means 3. Such visual field judging means 4 makes judgments according to kinds of perimetry, such as a screening perimetry, a threshold perimetry and an isopter perimetry.

In addition, the perimetry 1 according to the invention has fixation state judging means 5 for individually judging a fixation state of an examinee in association of each presented stimulus, and the fixation state judging means 5 individually judges the fixation state whenever the stimulus is presented. Preferably, the fixation state judging means 5 is comprised of a fixation state detecting portion 51 for detecting the fixation state of an examinee, a criterion output portion 52 for outputting judgment standards for judging the fixation state, a comparison judging portion 53 for judging the fixation state by comparing the signals from the fixation state detecting portion 51 and the criterion output portion 52, and a judged result outputting portion 54 for outputting the judgment results in association with each presented stimulus based upon the signals from the stimulus presentation means 2 and the comparison judging portion 53.

Preferably, the fixation state detecting portion 51 is comprised of a photographing portion, such as a infrared CCD, for obtaining successive images by photographing a front eye of an examinee. The fixation state detecting portion 51 may have an image processing portion for processing images obtained by the photographing portion in order to extract a pupil of an examinee and obtaining a center of the pupil, in addition to the photographing portion. A judgment of fixation state is described later, referring to FIG. 3. In addition, the fixation state detecting portion 51 may have a dislocation computing portion for computing a dislocation of a center of the pupil with respect to a standard position (that is, a central position of the pupil when an examinee correctly fixates the fixation target), in addition to the photographing portion and the image processing portion. In such a judgment of the fixation state, whether or not the computed dislocation is within a criteria (standard dislocation) may be only judged. Preferably, the fixation state detecting portion 51 detects before the stimulus presentation means 2 presents the stimulus (before presenting each stimulus, such detection is conducted separately). In addition, preferably, the image processing portion computes the center of the pupil twice or more times each presentation of the stimulus, and its average is computed.

If the criterion outputting portion 52 outputs one criterion, the comparison judging portion 53 judges to be "defective fixation" if a detected result by the fixation state detecting portion 51 exceeds the criterion, and judges to be "no defective fixation" if a detected result by the fixation state detecting portion 51 does not exceed the criterion. FIG. 3(a) is a typical view for explaining a way of judgment "defective fixation" or "no defective fixation" on the basis of a center position of a pupil (that is, the position of the center of the pupil computed by the image processing portion), and a reference number RV0 denotes the criterion outputted by the criterion outputting portion 52, and a reference number O denotes a standard position, that is, the central position of the pupil at the time when an examinee correctly fixates the fixation target. The judgment may be "no defective judgment" if the computed center of pupil is inside the criterion RV0, and may be "defective judgment" if the computed center of pupil is outside the criterion RV0. In such a judgment method, following two problems occur. That is, if "no defective fixation" is judged in place of "defective fixation" which is correct, defective data is used as measurement data and its measurement accuracy becomes low. On the contrary, "defective fixation" is judged in place of "no defective fixation" which is correct, effective data is thrown without use. Such problems can be solved on condition that the fixation state detecting portion 51 correctly detects.

Preferably, the criterion output portion 52 outputs two criterions, the first criterion and the second criterion (the first criterion is bigger than the second criterion) in order to avoid the above-mentioned two problems. FIG. 3(b) is a typical view for explaining a way of judging three, "defective fixation", "may be defective fixation" or "no defective fixation" from the central position of a pupil, that is, the central position of the pupil computed by the above-mentioned image processing portion. In the figure, a reference number RV1 denotes a first criterion and a reference number RV2 denotes a second criterion. In such a case, preferably, the comparison judging portion 53 judges "defective fixation" if a result of detection by the fixation state detecting portion 51 is higher than the first criterion (that is, the center of the pupil computed is outside of the first criterion RV1), and judges "may be defective fixation" if a result of detection by the fixation state detecting portion 51 is between the first criterion RV1 and the second criterion RV2 (that is, if the center of the pupil computed is between the first criterion RV1 and the second criterion RV2), and judges "no defective fixation" if a result of detection by the fixation state detecting portion 51 is lower than the second criterion (that is, the center of the pupil computed is inside of the second criterion RV2. In such a judgment, the fixation state detecting portion 51 seldom mistakes "no defective fixation" for "defective fixation" nor "defective fixation" for "no defective fixation" although the fixation state detecting portion 51 may mistake "may be defective fixation" for "defective fixation" or "no defective fixation" due to its rather low detection accuracy. For this reason, the above-mentioned two problems can be avoided. In the case of FIG. 3(b), there are two criterions, but it does not mean that three or more criterions are not exist in the invention.

The perimeter 1 according to the invention may have judgment processing means 6 for dealing with predetermined processes based upon the judgment results by the fixation state judging means 5. The processes by the judgment processing means 6 are (1) detection of defective fixation by stimulation of blind-spot if "defective fixation" is judged (2) display of a judgment result of a fixation state in connection with a stimulus as well as a judgment result of a visual field in connection with a stimulus (3) presentation of a stimulus for test after amending defective fixation, and (4) retry to test a measurement point where defective fixation was judged by presenting a stimulus again.

If the blind-spot is stimulated as shown in (1) mentioned before in such a case where two criterions are set, that is, the fixation state judging means judges each measurement point by three stages "defective fixation", "may be defective fixation" and "no defective fixation" on the basis of the two criterions, the judgment processing means 6 may control the stimulus presentation means 2 to detect the defective fixation by stimulating the blind-spot as follows.

The blind-spot is stimulated without fail in a measurement point where "defective fixation" was judged.

The blind-spot is stimulated at the first probability, such as 1/10, in the measurement point where "may be defective fixation" was judged.

The blind-spot is stimulated at the second probability well lower than the first probability, such as 1/30 (but, 0≦the second probability<the first probability) in the measurement point where "no defective fixation" was judged.

The blind-spot may not be stimulated if "no defective fixation" was judged.

In the case of the above-mentioned (2) process, the perimeter 1 according to the invention may have monitor means 7 to be controlled by the judgment processing means 6, and the monitor means 7 may display the judgment result of the visual field in connection with the stimulus A (each stimulus A displayed by the stimulus presentation means 2) and the judgment result of the fixation state in connection with the stimulus A (each stimulus A displayed by the stimulus presentation means 2). FIG. 4 is an example of such a display. In the figure, two digits of numerals denote a measurement result of each measurement point in a threshold perimetry, that is, the judgment result of the visual field in connection with each stimulus A, and a mark of square surrounding "27" is the stimulus which shows "defective fixation", and a double underline drawn under "32" denotes the stimulus which shows "may be defective fixation". In such a case where there are two criterions, that is, the judgment is executed by three stages "defective fixation", "may be defective fixation" and "no defective fixation" with two criterions, the monitor means 7 displays both the stimulus in the case of "defective fixation" and the stimulus in the case of "may be defective fixation", so that quantity of information increase.

If the fixation state judging means 5 judges "defective fixation" in the case of the above-mentioned (3) process, the judgment processing means 6 may control the stimulus presentation means 2 to regard a coordinate which the eye to be examined sees at this time as the coordinate of the fixation stimulus (the regarded fixation coordinate), and stimuli are presented from the regarded fixation coordinate to the coordinate where there is relatively no defective fixation so as to automatically amend the defective fixation.

If the fixation state judging means 5 judges "defective fixation" in the case of the above-mentioned (4) process, the judgment processing means 6 controls the stimulus presentation means 2 to present the stimulus again to the measurement point where "defective fixation" was judged for retry such point. The stimulus may be thus presented again after the test on all measurement points or at a proper timing during the test, that is, at a time when there are still remaining measurement points to be measured before finish of test on all measurement points. If the criterions are three or more, the processes (1) through (4) may be properly changed according to a number of the criterions.

In a case of the threshold perimetry with the perimeter according to the invention, it is necessary that a stimulus is presented to each measurement point two or more times, changing its luminance, and a threshold value is determined by presence of a reply from an examinee. In such a case, which stimulus (which presentation of stimulus) should be shown as "defective fixation" or "may be defective fixation" is necessary to be considered. If "good fixation and being responded", →"defective fixation and being responded"→"good fixation and being responded" succeed in such an order, the second defective fixation may be disregarded based on the last "good fixation and being responded". In such an example, a conclusion is the same if there is no response in all steps. In other words, if "being responded (or no response)" succeeds two or more times, the subject is the last fixation state in the respective response states (being responded or no response). In a general algorithm for determining the threshold value in a perimetry, the threshold value is determined by "being responded"→"no response"→"being responded" as shown in FIG. 6 ("○" in the figure means being responded and "X" means no response). For this reason, the subjects are the last stimulation through which the threshold value was determined and the stimulation just before the last stimulation since the last stimulation and the stimulation just before the last stimulation are always divided into "being responded" and "no response".

Preferably, a position of blind-spot is determined by a method disclosed in Japanese patent application publication No. 2008-36297 before the above-mentioned perimetry. In addition, the standard position as shown with a reference number O in FIGS. 3(a) and (b) (that is, the central position of the pupil when an examinee correctly fixates the fixation target) may be computed after determination of the position of blind-spot. Concretely speaking, it is preferable that a center position of a pupil is sampled so as to obtain an average and the average is the standard position.

Persons have respectively different rotation centers of eyeball. Then, preferably, an angle may be calibrated according to the following steps in order to eliminate a measurement error due to the different position of the rotation center of eyeball.

A stimulus is presented at a predetermined position in the visual field dome (may corresponds with an angle to be detected), and an examinee is invited to see the stimulus (see FIG. 5(a)).

A stimulus is presented two or more times, changing the position of the stimulus in up/down direction or in left/right direction.

A coordinate of a center position of a pupil is sampled during presentation of stimuli.

A coefficient of an angle of a CCD with respect to the coordinate is computed from an angle where stimuli are actually presented and the computed coordinate (see FIG. 5(b)).

For example, the criterions for judging "defective fixation" are as follows.

(a) An average size of a blind-spot is about 5°, so that the standard is ±2°
(b) Before perimetry, a size of a blind-spot of an examinee A (°) is measured, and the standard is ±A/2 (°)
(c) The standard is a deviation value from a standard deviation of a position sampled at the time of determination of the blind-spot position before perimetry, such as ±2α.

According to the invention, the fixation state is not judged in the whole perimetry, but the fixation state is individually judged for each stimulus in connection with each presented stimulus. In other words, the measurement point having high credibility and the measurement point having low credibility can be discriminated from each other. Then, even if defective fixation is judged, it is sufficient to retest only the point where the stimulus was presented, which was judged to be defective fixation. Therefore, examiner's burden and examinee's burden are lighter than a case where the whole test is retried from the first as a conventional way, and the test time is shorter and the test efficiency is improved thereby.

A structure of the stimulus presentation means 2 as shown in FIG. 2 is now briefly mentioned.

A reference numeral 20 in FIG. 2 denotes a stimulus presentation portion for presenting the stimulus A in the visual field of an examinee, a reference numeral 21 denotes an indicated position changing portion for changing an indicated position of the stimulus A, and a reference numeral 22 denotes a luminance setting portion for setting the stimulus A.

The stimulus presentation portion 20 as shown in the figure is comprised of a projection optical system 20A for projecting stimuli, and a projection member 20B to which the stimuli are projected by the projection optical system 20A. But, any structure of the stimulus presentation portion 20 is available as long as the stimuli are presented to the visual field of an examinee. For example, many LEDs may be located, and the LEDs may be selectively lightened. The projection member 20B as shown in FIG. 2 has a semi-sphere dome shape (visual field dome), but the other shape is available. For example, the shape having a curved surface excluding the semi-sphere face or the shape having a plane is also available.

In a case where the stimulus presentation portion 20 is comprised of the projection optical system 20A and the projection member 20B as shown in FIG. 2, the indicated position changing portion 21 may be comprised of driving means (not shown) for changing positions of structural elements of the projection optical system 20A, such as projector mirrors as shown with reference numerals 211, 212. On the other hand, in a case where the stimulus presentation portion is comprised of many LEDs, the indicated position changing portion may control which LEDs should be lightened. Even if the projection optical system or the LEDs is used, an examiner may manually instruct to change the position to be presented with a tough pen, a mouse or a keyboard, watching a display, or such an instruction may be automatically executed with a pre-composed program.

The luminance setting portion 22 may have various kinds of structures. But, the luminance setting portion 22 in FIG. 2 is comprised of rotatably supported turrets 221, 222 respectively having two or more filters which attenuances are different and drive mechanism 223 for changing positions of the turrets 221, 222.

The present invention has been explained on the basis of the example embodiments discussed. Although some variations have been mentioned, the embodiments which are described in the specification are illustrative and not limiting. The scope of the invention is designated by the accompanying claims and is not restricted by the descriptions of the specific embodiments. Accordingly, all the transformations and changes within the scope of the claims are to be construed as included in the scope of the present invention.

The invention claimed is:

1. A perimeter for measuring a visual field in a state that an examinee fixates a predetermined fixation point, comprising:
    stimulus presentation means for successively presenting stimuli having predetermined luminance at various positions in a visual field of an examinee;
    operation means to be operated by said examinee who perceived said presented stimulus;
    visual field judging means for judging said visual field of said examinee based on signals from said stimulus presentation means and said operation means; and
    fixation state judging means for individually judging fixation state of said examinee every said stimulus in connection with each presented stimulus whenever said stimulus is presented;
    said fixation state judging means including
        a fixation state detecting portion for detecting a fixation state of an examinee,
        a criterion outputting portion for outputting criterions for judgment of said fixation state,
        a comparison judging portion for judging said fixation state by comparing a signal from said fixation state detecting portion with a signal from said criterion outputting portion, and
        a judged result output portion for outputting a judged result in connection with each presented stimulus based upon signals from said stimulus presentation means and said comparison judging portion;
    said fixation state detecting portion having
        a photographing portion for obtaining successive images by photographing a front eye portion of an examinee and an image processing portion for processing said images obtained by said photographing portion so as to extract a pupil of said examinee and obtaining a center of said pupil;
    said criterion outputting portion having a first criterion for judging a fixation state based upon a position of said obtained center of said pupil and a second criterion that is smaller than said first criterion;

whereby said comparison judging portion judges "defective fixation" if said position of said center of said pupil obtained by said fixation state detecting portion is the first criterion or higher, and judges "may be defective fixation" if said position of said center of said pupil is between first criterion and said second criterion, and judges "no defective fixation" if said position of said center of said pupil is said second criterion or lower.

2. The perimeter according to claim 1, further comprising monitor means for displaying a judged result of a visual field in connection with each presented stimulus and a judged result of said fixation state in connection with each presented stimulus.

3. The perimeter according, to claim 1, further comprising judgment processing portion for controlling said stimulus presentation means to present a stimulus again to a measurement point where "defective fixation" was judged by said fixation state judging means.

4. The perimeter according to claim 1, further comprising judgment processing means for controlling said stimulus presentation means to detect defective fixation by stimulating a blind-spot on said measurement point where "defective fixation", "may be defective fixation" or "no defective fixation" was judged by said fixation state judging means, whereby a blind-spot is stimulated for said measurement point where "defective fixation" was judged without fail, a blind-spot is stimulated at a first probability for said measurement point where "may be defective fixation" was judged, and a blind-spot is stimulated at a second probability lower than said first probability for said measurement point where "no defective fixation" was judged.

* * * * *